United States Patent [19]

Maier

[11] Patent Number: 5,189,030
[45] Date of Patent: Feb. 23, 1993

[54] 1-AMINO-2-PHENYLETHANEPHOS-PHONIC ACIDS AS MICROBIOCIDES

[75] Inventor: Ludwig Maier, Arlesheim, Switzerland

[73] Assignee: Ciba-Geigy Corporation, Ardsley, N.Y.

[21] Appl. No.: 827,547

[22] Filed: Jan. 29, 1992

Related U.S. Application Data

[63] Continuation of Ser. No. 394,242, Aug. 14, 1989, abandoned, which is a continuation of Ser. No. 53,588, May 19, 1987, abandoned, which is a continuation of Ser. No. 870,577, Jun. 4, 1986, abandoned.

[30] Foreign Application Priority Data

Jun. 11, 1985 [CH] Switzerland .......................... 2462/85

[51] Int. Cl.$^5$ ........................... C07F 9/38; C07F 9/40; A61K 31/13; A61K 31/185
[52] U.S. Cl. .................................... 514/114; 558/166; 562/16
[58] Field of Search ............................. 514/114

[56] References Cited

U.S. PATENT DOCUMENTS

| | | | |
|---|---|---|---|
| 3,764,677 | 10/1973 | Kerst et al. ................... | 514/114 |
| 4,127,401 | 11/1978 | Colln et al. | |
| 4,147,780 | 4/1979 | Dingwall et al. ............ | 260/502.5 D |
| 4,182,758 | 1/1980 | Kamiya et al. ............... | 514/114 |
| 4,331,591 | 5/1982 | Baylis .......................... | 260/502.5 E |
| 4,379,146 | 4/1983 | Greenlee et al. ............ | 424/177 |
| 4,431,438 | 2/1984 | Hoyle et al. ................. | 260/502.5 D |
| 4,888,330 | 12/1989 | Cameron et al. ............ | 514/114 |

FOREIGN PATENT DOCUMENTS 112691 2/1982 Poland .

OTHER PUBLICATIONS

Chalmers et al, "J. Am. Chem. Soc." vol. 75 (1953) pp. 5278–5280.
Kafarski et al, "Chem. Abstracts", 98 (7) 54475a (1983).

Primary Examiner—Joseph E. Evans
Attorney, Agent, or Firm—Marla J. Mathias; Edward McC. Roberts

[57] ABSTRACT

Compounds of formula I

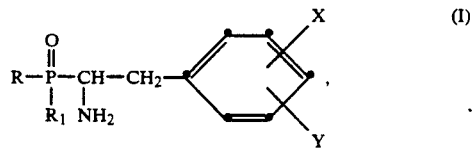

wherein R and $R_1$ are each independently $C_1$-$C_4$ alkoxy or hydroxy and X and Y are as defined herein, as well as the metal, ammonium or substituted ammonium salts thereof, are useful insecticides, acaricides and, in particular, fungicides. They can be applied to plants or to the locus thereof in the form of compositions or used as seed dressings.

3 Claims, No Drawings

1-AMINO-2-PHENYLETHANEPHOSPHONIC ACIDS AS MICROBIOCIDES

This application is a continuation of Ser. No. 394,242, filed Aug. 14, 1989, now abandoned, which in turn is a continuation of Ser. No. 053,588, filed May 19, 1987, now abandoned, which in turn is a continuation of Ser. No. 870,577, filed Jun. 4, 1986, now abandoned.

The present invention relates to microbicides containing as at least one active ingredient an 1-amino-2-arylethanephosphonic or 1-amino-2-arylethanephosphinic acid derivative or 1-amino-2-arylethanephosphine oxide derivative of formula I or a salt thereof, and to the use of these compounds for controlling harmful micro-organisms.

The compounds of the present invention have the formula

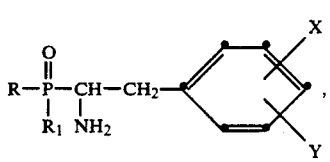

wherein R and $R_1$ are each independently of the other $C_1$-$C_4$alkyl, $C_4$-$C_4$alkoxy or hydroxy, X is hydrogen, halogen, $C_1$-$C_4$alkyl, $C_1$-$C_4$-alkoxy, trimethylsilyl, cyano, methoxycarbonyl or the radical —$CH_2$—$CH(NH_2)$—$P(O)(R)(R_1)$, and Y is hydrogen, halogen, $C_1$-$C_2$-haloalkoxy or $C_1$-$C_2$haloalkyl, and salts thereof if R and/or $R_1$ are hydroxy.

Formula I expresses ethanephosphonic acid derivatives if R and $R_1$ are hydroxy or alkoxy, ethanephosphinic acid derivatives if one of the two substiturnts R and $R_1$ is alkyl, and ethanephosphine oxide derivatives if both substituents R and $R_1$ are alkyl.

$C_1$-$C_4$Alkyl by itself or as moiety of an alkoxy group is methyl, ethyl, propyl, isopropyl, n-butyl, sec-butyl, isobutyl or tert-butyl.

Halogen denotes fluorine, chlorine, bromine or iodine. $C_1$-$C_2$Haloalkyl by itself or as moiety of a haloalkoxy group is a monohalogenated methyl or ethyl group or a methyl or ethyl group which is perhalogenated by a specific halogen atom or by different halogen atoms. Typical examples are $CHCl_2$, $CHF_2$, $CH_2Cl$, $CCl_3$, $CH_2F$, $CHBr_2$, $CH_2CH_2Cl$, $CHCl$—$CHCl$, $CF_3$, $C_2F_5$, $CF_2Cl$, $CF_2$—$CF_2Cl$.

Salts of a free hydroxyl group are unsubstituted or substituted ammonium or hydrazinium salts or metal cations.

Examples of metal ions are the cations of the following elements: alkali metals such as lithium, sodium or potassium; alkaline earth metals such as magnesium, calcium, strontium or barium; elements of the first to the eighth Periodic auxiliary group such as chromium, manganese, iron, cobalt, nickel, copper, zinc, silver, with iron, manganese, copper and zinc being preferred; elements of the third and fourth Periodic main group such as aluminium, silicon, tin, lead, zirconium, titanium, preferably aluminium, which metal ions may be present in the salts or complexes of formula I in the valence states appropriate to them.

Phosphonic acid derivatives of formula I can in principle be obtained by reacting an unsubstituted or substituted 2-phenylacetaldehyde with ammonia and a dialkyl phosphite, followed by optional subsequent hydrolysis with a mineral acid:

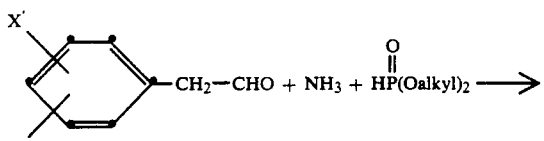

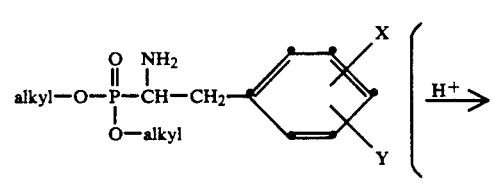

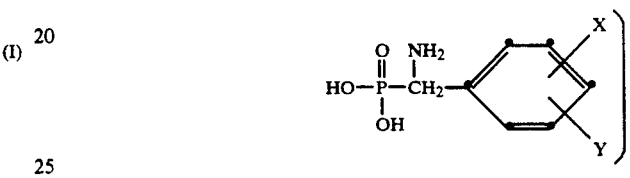

[Chalmers and Kosolapoff, J.Am.Chem.Soc. 75, 5278 (1953)].

A mineral acid will be understood as meaning preferably a hydrohalic acid such as hydrochloric or hydrobromic acid, sulfuric acid, phosphoric acid, nitric acid, toluenesulfonic acid and the like.

A rather more general method is that proposed by Berlin et al., [J. Org. Chem. 33, 3090, (1968)], in which a substituted phenylacetylhalide is reacted with a) O,O,O-trialkylphosphite, b) O,O-trialkylphosphonite or c) O-trialkylphosphinite, and the intermediate is further reacted, in the present of hydroxylamine, to give the phosphonyl, phosphinyl or oxophosphino-oxime, from which the amine can be obtained by hydrogenation:

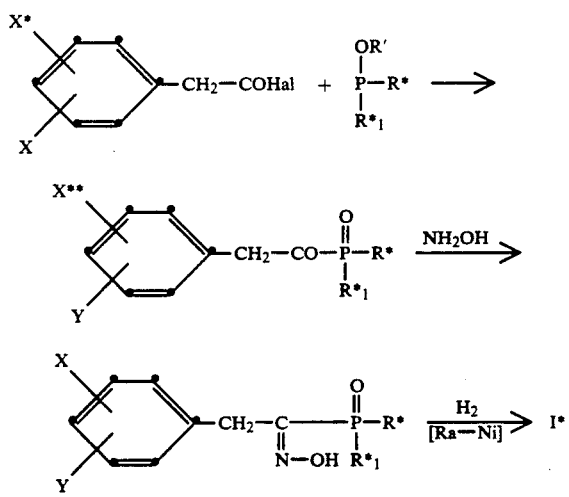

In the above formulae, X and Y are as defined for formula I, and the remaining substituents are defined as follows:
  X′=H, halogen, $C_1$-$C_4$alkyl, $C_1$-$C_4$alkoxy, $Si(CH_3)_3$, —CN, —$COOCH_3$ or —$CH_2$—CHO,
  alkyl=$C_1$-$C_4$alkyl, X*=H, halogen, $C_1$-$C_4$alkyl, $C_1$-$C_4$alkoxy, Si($CH_3$)$_3$, —CN, —COOCH$_3$ or —CH$_2$—COHal, X**=H, halogen, $C_1$-$C_4$alkyl, $C_1$-$C_4$alkyoxy, Si($CH_3$)$_3$, —CN, —COOCH$_3$ or —CH$_2$—C(O)—P(O) R* (R*$_1$), Hal=halogen, preferably Cl or Br, R'=$C_1$-$C_4$alkyl, R*=$C_1$-$C_4$alkyl or $C_1$-$C_4$alkoxy, R*$_1$=$C_1$-$C_4$alkyl or $C_1$-$C_4$alkoxy.

Formula I* embraces only those compounds of formula I, wherein R and R$_1$ have the meaning of R* and R*$_1$. Where R* and/or R*$_1$ are $C_1$-$C_4$alkoxy, free hydroxyl groups can be obtained therefrom by hydrolysis with, preferably, a mineral acid. Free OH groups can, if desired, be converted with a base into salts, e.g. metal salts, ammonium salts, alkylammonium salts, dialkylammonium salts or the like.

Compounds of formula I can be obtained in simple manner and in high yield by a further method by aralkylating the activated Schiff's base obtained from a) aminomethylphosphonate, aminomethylphosphinate or aminomethylphosphine oxide, and b) an aldehyde such as benzaldehyde or a ketone such as phenylacetone or benzophenone, with a suitably substituted benzyl halide [R. W. Radcliffe and B. G. Christensen, Tetrahedron Letters, 4645 (1973)]:

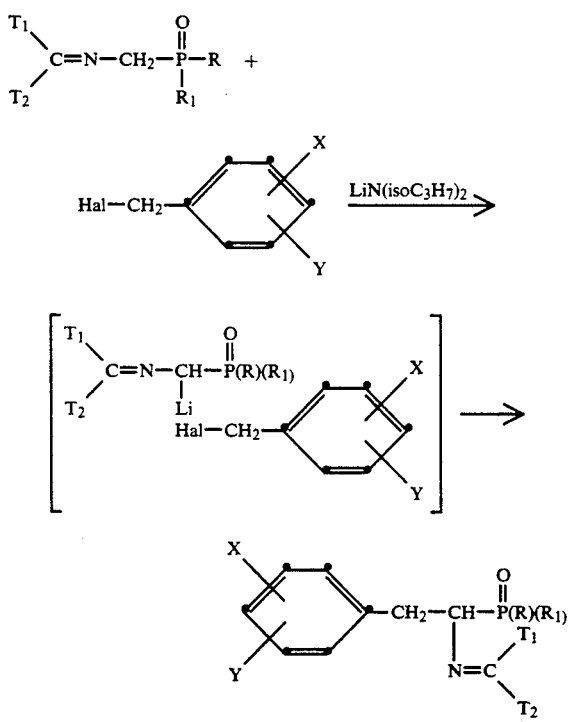

Hal=halogen, preferably Br or Cl.

The activation of the —CH$_2$— group vicinal to the P-atom in the starting material can also be effected by other reagents such as butyllithium or sodium hydride in e.g. tetrahydrofuran. R, R$_1$, X and Y are as defined for formula I, T$_1$ is hydrogen or an aliphatic or aromatic radical and T$_2$ is an aliphatic or aromatic radical.

The last step of the hydrogenolytic cleavage of the Schiff's base to obtain the desired final product of formula I is carried out by catalytic cleavage with e.g. H$_2$/Pd/C, but can also be performed with hydrogen in the presence of other catalysts (such as platinum or Pt/C). In the presence of a mineral acid such as hydrochloric or hydrobromic acid, it is possible to carry out the cleavage of the Schiff's base and the hydrolysis of an alkoxy group to a hydroxyl group—provided at least one of the substituents R and/or R$_1$ is alkoxy—at elevated temperature (40°-150° C.) in one reaction step. It is advantageous to use inert solvents or diluents in all the aforementioned procedures. Examples of customary solvents and diluents are aliphatic and aromatic hydrocarbons such as benzene, toluene, xylenes, petroleum ether; halogenated hydrocarbons such as chlorobenzenes, methylene chloride, ethylene chloride, chloroform, tetrachloroethylene; ethers and ethereal compounds such as dialkyl ethers (diethyl ether, diisopropyl ether, tert-butylmethyl ether and the like), anisole, dioxane, tetrahydrofuran; nitriles such as acetonitrile, propionitrile, and mixtures of such solvents with one another.

The reaction temperature during the aralkylation (benzylation) is normally in the range from −100° to +10° C., preferably from −80° to −20° C. The hydrogenolytic cleavage is conveniently carried out in the temperature range from −20° to +80° C.

The cited starting compounds are known or are prepared by methods known per se. To prepare the Schiff's base, it is advantageous to carry out the process in an inert gas such as nitrogen or argon. Substituted benzyl bromides can be readily obtained from suitably substituted toluenes by bromination with N-bromosuccinimide in CCl$_4$ in the presence of azoisobutyronitrile (catalyst).

The compounds of formula I are phosphonyl, phosphinyl and oxophosphino analogs of β-phenylalanine. As such they possess, adjacent to the P-atom, an asymmetrical carbon atom, such that the structures corresponding to the natural L-α-amino acids have the (R)-configuration, whereas the structures of formula I corresponding to the D-α-amino acids have the (S)-configuration. The respective (R)- or (S)-configurations of a diastereoisomeric (R,S)-compound can be obtained pure therefrom by fractional crystallisation or chromatography (HPLC). The (R)-diastereoisomers and (S)-diastereoisomers have different microbicidal properties.

The present invention also relates to the above preparatory methods, where these lead to novel compounds. The invention further relates to the novel compounds of formula I in which at least one of the substituents X and Y has a meaning different from hydrogen, provided R and R$_1$ are simultaneously hydroxy or ethoxy.

Compounds of formula I, wherein R and R$_1$ are $C_1$-$C_4$ alkoxy, are valuable acaricides (in particular against Tetranychus and Amblyomma species) as well as insecticides which are effective in particular against sucking insects (aphicides).

Preferred microbicides are compounds of formula I and salts thereof, wherein

R is $C_1$-$C_4$alkyl or OH,

R$_1$ is OH,

X is hydrogen, halogen, $C_1$-$C_4$alkyl, $C_1$-$C_4$alkoxy, Si($CH_3$), —CN, —COOCH$_3$ or CH$_2$—CH(NH$_2$)—P(O)(R)(R$_1$), and Y is hydrogen, halogen, halomethoxy, haloethoxy or halomethyl.

Among these microbicides, those compounds are preferred wherein

R=R$_1$=OH,

X is hydrogen, fluorine, chlorine or bromine, $C_1$-$C_4$alkyl, $CH_3O$, $Si(CH_3)_3$, —CN, —COOCH$_3$ or —CH$_2$—CH(NH$_2$)—P(O)(OH)$_2$, and Y is fluorine, chlorine, bromine, halomethoxy or halomethyl.

Among these last mentioned microbicides, those compounds are particularly preferred in which at least one of the substituents X and Y is or contains halogen, and, of these, those compounds in which one of the substituents X and Y is or contains fluorine.

Another important subgroup of microbicidally active compounds are those compounds of formula I and salts thereof wherein R and $R_1$ are each independently of the other $C_1$-$C_4$alkyl, $C_1$-$C_4$alkoxy or hydroxy, X is halogen, $C_1$-$C_4$alkyl, $C_1$-$C_4$alkoxy, $Si(CH_3)_3$, cyano or —CH$_2$—CH(NH$_2$)—P(O)(R)(R$_1$), Y is hydrogen, halogen, halomethoxy, haloethoxy or halomethyl.

Among these last mentioned microbicides, those compounds are especially important wherein R, $R_1$ and Y have the given meanings and X is fluorine, chlorine, methyl, ethyl, isopropyl, tert-butyl, methoxy, ethoxy, isopropoxy or cyano.

Also important are microbicidal compounds and salts thereof in which R and $R_1$ are as defined for formula I, X is halogen, methyl, methoxy or cyano, and Y is hydrogen, halogen, OCHF$_2$ or CF$_3$.

Another important group of microbicides comprises those compounds of formula I, wherein R and $R_1$ are as previously defined, X is hydrogen and Y is difluoromethoxy or trifluoromethyl.

Derivatives of peptidylaminomethanephosphonic and peptidylaminophosphinic acid are disclosed in U.S. Pat. No. 4,016,148 as potentiators for antibiotics. However, no particulars relating to pest control are contained therein and such utility is in no way suggested.

Peptidylaminoalkanephosphonic acid derivatives are proposed as herbicides and retarders for plant growth and plant emergence in U.S. Pat. No. 4,431,438. However, there is no mention of protecting plants against microbial attack. It must also be added that compositions with general herbicidal or growth inhibiting properties are of necessity very poorly suited to protecting cultivated plants.

Surprisingly, it has now been found that the aminoethanephosphonic acid derivatives of formula I and salts thereof not only have no herbicidal properties, but have an unexpectedly potent microbicidal activity which is particularly suitable for imparting lasting protection to plants from attack by fungi and bacteria and for promoting the development of said plants.

Provided at least one of the substituents R and $R_1$ is an OH group, the salts of formula I come into the category of preferred compounds. Especially preferred on account of their fungicidal activity are the metal salts, in particular the aluminium, nickel, manganese and copper salts and the lower alkylammonium salts of formula I, which are particularly suitable for soil application and as seed dressing agent.

The principal utility of compounds of formula I is for controlling harmful phytopathogenic fungi. Thus the compounds of formula I have, for practical purposes, a very useful curative, preventive and systemic action for protecting cultivated plants without adversely affecting said plants by undesirable side-effects. Examples of cultivated plants within the scope of this invention are: cereals (wheat, barley, rye, oats, rice); beet (sugar beet and fodder beet), drupes, pomes and soft fruit (apples, pears, plums, peaches, almonds, cherries, strawberries, raspberries and blackberries), leguminous plants (beans, lentils, peas, soybeans); oil plants (rape, mustard, poppy, olives, sunflowers, coconuts, castor oil plants, cocoa beans, groundnuts); cucumber plants (cucumber, marrows, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); or plants such as maize, tobacco, nuts, coffee, sugar cane, tea, vines, hops, bananas, avocados, and natural rubber plants, as well as ornamentals.

With the compounds of formula I it is possible to inhibit or destroy the micro-organisms which occur in plants or parts of plants (fruit, blossoms, leaves, stems, tubers, roots) in these and in related crops of useful plants, while at the same time the parts of plants which grow later are also protected from attack by such micro-organisms.

The compounds of formula I are particularly effective against the phytopathogenic fungi belonging to the following classes: Ascomycetes (e.g. Helminthosporium and Fusarium species) and Basidomycetes (e.g. Tilletia and Ustilago). The compounds of formula I can therefore also be used as seed dressing agents for protecting seeds (fruit, tubers, grains) and plant cuttings against fungus infections as well as against phytopathogenic fungi which occur in the soil.

Accordingly, the invention also relates to the use of compounds of formula I for controlling phytopathogenic micro-organisms and for the preventive treatment of plants to protect them from attack by such microorganisms.

The compounds of formula I are normally applied in the form of compositions and can be applied to the crop area or plant to be treated, simultaneously or in succession, with further compounds. These compounds can be both fertilisers or micronutrient donors or other preparations that influence plant growth. They can also be selective herbicides, fungicides, bactericides, nematicides, molluscicides or mixtures of several of these preparations, if desired together with further carriers, surfactants or application promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers.

The compounds of the formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymeric substances. As with the nature of the compositions, the methods of application, such as spraying, atomising, dusting, scattering or pouring, are chosen in accordance with the intended objectives and the prevailing circumstances. Advantageous rates of application in agriculture are normally from 50 g to 5 kg of active ingredient (a.i.) per hectare, preferably from 100 g to 2 kg a.i./ha, most preferably from 100 g to 600 g a.i./ha.

Suitable solvents are: aromatic hydrocarbons, preferably the fractions containing 8 to 12 carbon atoms, e.g.

xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethylsulfoxide or dimethylformamide, as well as epoxidised vegetable oils such as epoxidised coconut oil or soybean oil; or water.

Particularly useful application-promoting adjuvants which are able to reduce substantially the rate of application are also natural (animal or vegetable) or synthetic phospholipids of the series of the cephalins and lecithins, e.g. phosphatidyl ethanolamine, phosphatidyl serine, phosphatidyl glycerol or lysolecithin.

Depending on the nature of the compound of the formula I to be formulated, suitable surface-active compounds are nonionic, cationic and/or anionic sufactants having good emulsifying, dispersing and wetting properties. The term "surfactants" will also be understood as comprising mixtures of surfactants.

The surfactants customarily employed in the art of formulation are described e.g. in "McCutcheon's Detergents and Emulsifiers Annual", MC Publishing Corp. Ridgewood, N.J., 1981; Helmut Stache "Tensid-Taschenbuch" (Surfactant Handbook) Carl Hanser Verlag, Munich/Vienna, 1981; M. and J. Ash, Encyclopedia of Surfactants, Vol I-III, Chemical Publishing Co., New York, 1980–1981.

The agrochemical compositions usually contain 0.1 to 99%, preferably 0.1 to 95%, of a compound of formula I, 99.9 to 1%, preferably 99.8 to 5%, of a solid or liquid adjuvant, and 0 to 25%, preferably 0.1 to 25%, of a surfactant.

Whereas commercial products are preferably formulated as concentrates, the end user will normally employ dilute formulations.

The invention is illustrated in more detail by the following Examples, without implying any restriction to what is described therein. Parts and percentages are by weight.

PREPARATORY EXAMPLES

Example 1

Preparation of O,O-diisopropyl-1-amino-2-(4-(fluorophenyl)ethylphosphonate of Formula

[compound 1.8]

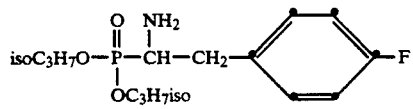

a) Preparation of O,O-diisopropyl-1-N-benzylidenamino-2-(4-fluorophenyl)ethylphosphonate (intermediate)

With stirring and cooling, 500 ml of n-butyllithium are added to 113.4 g (0.8 mole) of diisopropylamine in 750 ml of tetrahydrofuran (THF). The mixture is cooled to −75° C. and then a solution of 226.6 g (0.8 mole) of O,O-diisopropylbenzylideneaminomethanephosphonate in 600 ml of THF is added dropwise over the course of 1 hour. After stirring for 1 hour, a solution of 151.2 g (0.8 mole) of 4-fluorobenzyl bromide in 150 ml of THF is added dropwise and stirring is continued for 1 hour. After the reaction mixture has stood overnight at room temperature, the solvent is stripped off and the residue is dissolved in 1 liter of dichloromethane. The solution is washed with three 200 ml portions of water and dried over $Na_2SO_4$. The solvent is then removed by evaporation to give 286.3 g (91.4% of theory) of the intermediate, which yields 261.2 g (83.4% of theory) of pure product after molecular distillation. Boiling point: 160° C./0.1 mbar.

b) Preparation of the Final Product

To a solution of 19.6 g (0.05 mole) of the intermediate obtained in 1a) in 200 ml of isopropanol are added 2 g of Pd/C (5% Pd) and the mixture is hydrogenated at room temperature (20°–25° C.). After 62% hydrogen uptake, 2 g of Pd/C are again added and, after 90% hydrogen uptake, a further 2 g of Pd/C are added. The hydrogen uptake is complete after 19 hours. The reaction mixture is filtered and the filtrate is concentrated by rotary evaporation. The residue (ca. 15 g) is distilled in a bomb tube, affording 12.6 g (83.1% of theory) of pure final product in the form of a colourless oil with a boiling point of 170° C./0.08 mbar.

Example 2

Preparation of 1-amino-2-(4-fluorophenyl)ethanephosphonic acid (compound 2.6)

A mixture of 227.5 g (0.75 mole) of O,O-diisopropyl-1-amino-2-(4-fluorophenyl)ethylphosphonate and 750 ml of 20% hydrochloric acid is refluxed, with stirring, for 5 hours and stirred for a further 5 hours at room temperature. After addition of 500 ml of water, the precipitate is filtered and washed with 250 ml of water and 500 ml of methanol. Yield: 103.3 g of title compound. The filtrate is concentrated and the residue is recrystallised from methanol/propylene oxide, affording a further 43.3 g of final product.

Total yield: 146.6 g (89.2% of theory).

Melting point: 266°–270° C. (dec.).

Example 3

Preparation of the optical isomers of 1-amino-2-(4-fluorophenyl)ethanephosphonic acid A. Preparation of the dibenzoyl tartrates of O,O-diethyl-1-amino-2-(4-fluorophenyl)ethylphosphonate

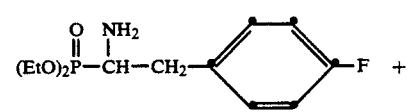

a) To a solution of 68.82 g (0.125 mole) of O,O-diethyl-1-amino-2-(4-fluorophenyl)ethylphosphonate in 750 ml of methanol and 750 ml of ethanol are added 47.04 g of dibenzoyltartaric acid (L)(−)x$H_2O$. After stirring for 2 hours, the thick white suspension is filtered and the residue is dried. Two recrystallisations from ethanol yield 31.5 g (39.8% of theory) of "salt I" of m.p. 179° C. (dec.);

$[\alpha]_D^{20} = -66.4° \pm 0.5°$ (c=2.077% in methanol).

b) The combined residual filtrates are evaporated and the residue is stirred in 1N NaOH. The solution is saturated with sodium chloride and extracted with three 400 ml portions of $CH_2Cl_2$. The organic phase is dried over $Na_2SO_4$ and concentrated by evaporation. The residual brown oil (37.5 g) is dissolved in 400 ml of methanol and 400 ml of ethanol and 25.6 g of dibenzoyltartaric acid (D)(+)x$H_2O$, are added to the solution. After stirring for 2 hours, 63 g of salt are isolated by filtration and recrystallised from 1200 ml of methanol to give 7.2 g of crude "salt II". The filtrate is concentrated and the residue recrystallised from 500 ml of ethanol, affording 17 g of pure "salt II";

$[\alpha]_D^{20} = +67.3° \pm 0.5°$ (c = 1.998% in methanol).

B.

a) Preparation of (+) O,O-diethyl-1-amino-2-(4-fluorophenyl)ethylphosphonate 25.34 g of salt I are stirred for 2 hours at room temperature in 100 ml of 1N NaOH to effect liberation from the tartrate. The clear solution is saturated with sodium chloride, then 200 ml of $CH_2Cl_2$ are added and the resultant suspension is filtered in vacuo. The residue is washed with two 200 ml portions of $CH_2Cl_2$. The organic phase of the combined filtrates is separated, dried over $Na_2SO_4$, filtered, and concentrated by evaporation to give 9.1 g (82.7% of theory) of the desired final product as a pale yellow oil;

$[\alpha]_D^{20} = +10.6° \pm 0.4°$ (c = 2.5% in methanol).

$^1$H-NMR in $CDCl_3$: 1.3 ($NH_2$, $CH_3$) (t, 8H); 2.3–3.5 (PCH—$CH_2$) (m, 3H); 4.17 ($OCH_2$) (qu, 4H); 7.1 (m) (4H, phenyl).

b) Preparation of (+) 1-amino-2-(4-fluorophenyl)ethanephosphonic acid 5.51 g (0.02 mole) of the (+) phosphonate obtained in a) are refluxed in 40 ml of 20% hydrochloric acid for 4 hours. The solution is then concentrated and the residue is recrystallised from methanol/propylene oxide, affording 3.7 g (84.5% of theory) of the desired final product.

Melting point: 259°–263° C. (dec.);

$[\alpha]_D^{20} = +37.5° \pm 0.4°$ (c = 2.636% in 1N NaOH).

$^1$H-NMR in $D_2O$/NaOD: 2.3–3.1 (PCH—$CH_2$) (m, 3H); 4.65 (OH, $NH_2$) (s); 6.6–7.1 (phenyl, 4H) (m).

C.

a) Preparation of (−) O,O-diethyl-1-amino-2-(4-fluorophenyl)ethylphosphonate in accordance with the method of Ba) from "salt II" with 1N NaOH solution.

Yield: 95.9% of theory. Pale yellow oil $[\alpha]_D^{20} = -10.3° \pm 0.5°$ (c = 2.036 in methanol).

b) Preparation of (−) 1-amino-2-(4-fluorophenyl)ethanephosphonic acid in accordance with the method of Bb) by hydrolysis of the above (−) phosphonate in 20% hydrochloric acid.

Yield: 77.6% of theory.

Melting point: 261°–263° C. (dec.).

$[\alpha]_D^{20} = -36.9° \pm 0.5°$ (c = 2.081% in 1N NaOH).

$^1$H-NMR in $D_2O$/NaOD: 2.5–3.4 (PCH—$CH_2$) (m, 3H); 4.85 (OH, $NH_2$) (s); 6.8–7.4 (phenyl, 4H) (m).

The following compounds of formula I, which are obtained as mixtures of diastereoisomers unless otherwise specifically mentioned, can also be prepared in this manner or by one of the other methods described above.

The $^1$H-NMR values were determined with a Varian EMK-360 spectrometer at 60 MHz in $CDCl_3$ with $(CH_3)_4Si$ as reference substance.

The $^{31}$P-NMR values were recorded with a Bruker WP 80 spectrometer at 32.28 MHz with 85% $H_3PO_4$ (externally) as reference substance.

Key:
Me = methyl
Et = ethyl
iPr = isopropyl
The temperatures are given in degrees centigrade.

TABLE 1

Compounds of formula 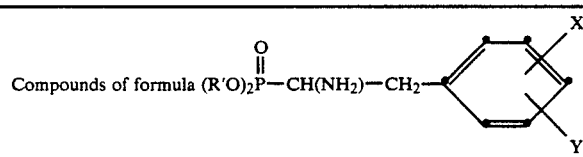

| Compound | R' | X | Y | Physical data |
|---|---|---|---|---|
| 1.1 | Et | H | H | b.p. 170°/0.6 mbar |
| 1.2 | iPr | H | H | $^1$H: 1.3($NH_2$), 2.5–3.5(PCH—$CH_2$) 7.3 (aromatic-H) |
| 1.3 | Et | 4-Cl | H | $n_D^{20}$ 1.5140 |
| 1.4 | Et | 3-Cl | H | $^1$H: 1.3; 2.4–3.5; 7.2 |
| 1.5 | Et | 4-Br | H | b.p. 125°/0.05 mbar |
| 1.6 | Et | 4-I | H | $^1$H: 1.3; 2.3–3.4; 7.767 |
| 1.7 | Et | 4-F | H | b.p. 150–160°/0.08 mbar |
| 1.8 | iPr | 4-F | H | b.p. 170°/0.08 mbar |
| 1.9 | iPr | 3-F | H | b.p. 150°/0.05 mbar |
| 1.10 | iPr | 2-F | H | b.p. 150°/0.08 mbar |
| 1.11 | Et | 2-Cl | 4-Cl | m.p. 59–62° |
| 1.12 | Et | 3-Cl | 4-Cl | $n_D^{20}$ 1.5272 |
| 1.13 | Et | 4-Me | H | $^1$H: 1.4; 2.5–3.5; 7.15; 2.32 (X = $CH_3$). $^{31}$P: 28.09 |
| 1.14 | Et | 3-Me | H | $n_D^{20}$ 1.5060 |
| 1.15 | Et | 2-Me | H | $^1$H: 1.33; 2.5–3.5; 7.2; 2.33 (X = $CH_3$). $^{31}$P: 28.19 |
| 1.16 | Et | 3-$CF_3$ | H | $n_D^{20}$ 1.4659 |
| 1.17 | iPr | 4-t-butyl | H | b.p. 140°/0.01 mbar |
| 1.18 | Et | 4-MeO | H | b.p. 165°/0.2 mbar |
| 1.19 | Et | 2-MeO | H | b.p. 125°/0.1 mbar |
| 1.20 | Et | 2-F | 6-Cl | |
| 1.21 | Et | H | 4-$OCHF_2$ | |

TABLE 1-continued

Compounds of formula 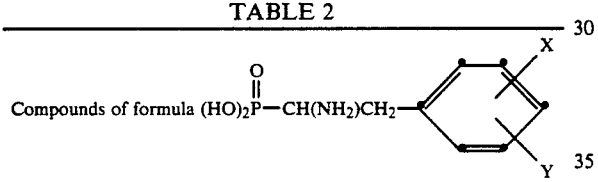

| Compound | R' | X | Y | Physical data |
|---|---|---|---|---|
| 1.22 | Et | H | 3-OCHF$_2$ | |
| 1.23 | iPr | H | 4-OCHF$_2$ | |
| 1.24 | iPr | H | 4-CF$_3$ | |
| 1.25 | iPr | H | 4-CHF$_2$ | |
| 1.26 | Et | H | 4-OC$_2$F$_5$ | |
| 1.27 | Et | H | 4-OCF$_2$—CF$_2$Cl | |
| 1.28 | Et | 2-Si(Me)$_3$ | H | b.p. 110°/0.1 mbar |
| 1.29 | Et | 3-Si(Me)$_3$ | H | b.p. 150°/0.12 mbar |
| 1.30 | Et | 4-Si(Me)$_3$ | H | b.p. 120°/0.1 mbar |
| 1.31 | iPr | 4-CN | H | $^1$H: 1.35; 2.6–3.5; 7.4–7.6 |
| 1.32 | Et | 3-F | 4-F | b.p. 115°/0.1 mbar |
| 1.33 | Et | 2-F | 4-F | b.p. 110°/0.08 mbar |
| 1.34 | iPr | 2-Cl | 3-Cl | b.p. 160°/0.1 mbar |
| 1.35 | iPr | 3-I | H | |
| 1.36 | iPr | 4-COOCH$_3$ | H | b.p. 160°/0.08 mbar |
| 1.37 | Et | 4-CH$_2$—CH—(NH$_2$)—P(O)—(OEt)$_2$ | H | |
| 1.38 | Et | 2-Cl | 4-F | |
| 1.39 | Et | 2-F | 6-F | b.p. 105°/0.1 mbar |
| 1.40 | Et | 2-F | H | b.p. 95°/0.1 mbar |

TABLE 2

Compounds of formula 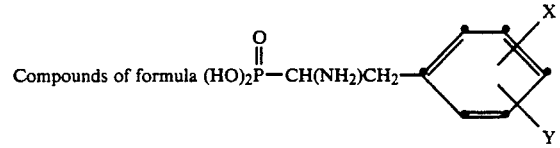

| Compound | X | Y | Melting point (m.p.) [dec.] |
|---|---|---|---|
| 2.1 | H | H | 278–282 |
| 2.2 | 4-Cl | H | 280–282 |
| 2.3 | 3-Cl | H | 268–272 |
| 2.4 | 4-Br | H | 284–286 |
| 2.5 | 4-I | H | 255–259 |
| 2.6 | 4-F | H | 266–270 |
| 2.7 | 3-F | H | 278–280 |
| 2.8 | 2-F | H | 275–276 |
| 2.9 | 2-Cl | 4-Cl | 279–280 |
| 2.10 | 3-Cl | 4-Cl | 274–278 |
| 2.11 | 4-Me | H | 276–279 |
| 2.12 | 3-Me | H | 270–273 |
| 2.13 | 2-Me | H | 244–245 |
| 2.14 | H | 3-CF$_3$ | 258–262 |
| 2.15 | 4-t-butyl | H | 264–268 |
| 2.16 | 4-OMe | H | |
| 2.17 | 2-OMe | H | |
| 2.18 | 2-F | 6-Cl | |
| 2.19 | H | 4-OCHF$_2$ | 232–236 |
| 2.20 | H | 3-OCHF$_2$ | |
| 2.21 | H | 4-CF$_3$ | |
| 2.22 | H | 4-CHF$_2$ | |
| 2.23 | H | 4-OC$_2$F$_5$ | |
| 2.24 | H | 4-OCF$_2$—CF$_2$Cl | |
| 2.25 | 2-Si(Me)$_3$ | H | |
| 2.26 | 3-Si(Me)$_3$ | H | |
| 2.27 | 4-Si(Me)$_3$ | H | |
| 2.28 | 4-CN | H | 267–269 |
| 2.29 | 3-F | 4-F | |
| 2.30 | 2-F | 4-F | 271–274 |
| 2.31 | 2-Cl | 3-Cl | |
| 2.32 | 3-I | H | |
| 2.33 | 4-CH$_2$—CH(NH$_2$)—P(O)(OH)$_2$ | H | |
| 2.34 | 2-Cl | 4-F | |
| 2.35 | 3-Me | 4-Cl | |
| 2.36 | 2-Me | 4-F | |
| 2.37 | 2-F | 6-F | 258–261 |

TABLE 3

Compounds of formula R—P(=O)(OH)—CH(NH$_2$)—CH$_2$—aryl(X,Y)

| Compound | R | X | Y | m.p. [dec.] |
|---|---|---|---|---|
| 3.1 | Me | H | H | 261–262 |
| 3.2 | Et | 2-Me | H | 234–235 |
| 3.3 | Et | 3-Me | H | 229–232 |
| 3.4 | Et | 4-Me | H | 233–236 |
| 3.5 | Me | 4-F | H | 254–257 |
| 3.6 | Me | 4-Br | H | 254–257 |
| 3.7 | Me | 4-Cl | H | 242–245 |
| 3.8 | Me | 3-Me | H | 260–262 |
| 3.9 | Et | H | H | 230–231 |
| 3.10 | Me | 3-Cl | H | |
| 3.11 | Me | 3-F | H | |
| 3.12 | Me | 2-F | H | |
| 3.13 | Et | 2-F | 6-Cl | |
| 3.14 | Me | 2-Cl | 4-Cl | |
| 3.15 | Me | 3-Cl | 4-Cl | |
| 3.16 | Et | 2-Cl | 3-Cl | |
| 3.17 | Me | H | 3-CF$_3$ | |
| 3.18 | Me | H | 4-OCHF$_2$ | |
| 3.19 | Me | 4-OC$_2$H$_5$ | H | |
| 3.20 | Me | 4-t-butyl | H | |
| 3.21 | Me | H | 4-OC$_2$F$_5$ | |

TABLE 3-continued

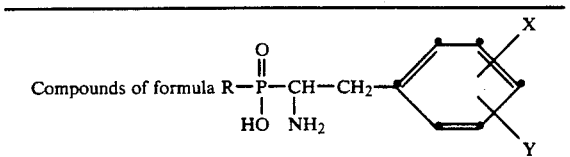

Compounds of formula

| Compound | R | X | Y | m.p. [dec.] |
|---|---|---|---|---|
| 3.22 | Et | 2-Cl | 4-F | |

TABLE 4

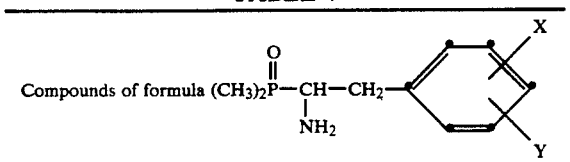

Compounds of formula $(CH_3)_2\overset{O}{\underset{\|}{P}}-CH-CH_2-\text{[aryl]}$ with $NH_2$

| Compound | X | Y | Physical data |
|---|---|---|---|
| 4.1 | H | H | b.p. 160–170°/0.05 mbar |
| 4.2 | 4-F | H | |
| 4.3 | 4-Cl | H | |
| 4.4 | 2-Cl | 4-Cl | |
| 4.5 | 2-Cl | 4-F | |
| 4.6 | H | 4-OCHF$_2$ | |
| 4.7 | H | 3-CF$_3$ | |
| 4.8 | 4-t-butyl | H | |
| 4.9 | 4-CN | H | |
| 4.10 | 4-Si(Me)$_3$ | H | |
| 4.11 | 4-OMe | H | |
| 4.12 | 4-OMe | 2-Cl | |
| 4.13 | H | 3-OCHF$_2$ | |
| 4.14 | 2-Me | H | b.p. 160°/0.05 mbar |
| 4.15 | 2-Me | 4-Cl | |
| 4.16 | 3-Me | 2-Cl | |
| 4.17 | 3-Me | H | b.p. 160°/0.07 mbar |
| 4.18 | 4-Me | H | b.p. 150–55°/0.1 mbar |
| 4.19 | H | 4-OC$_2$F$_5$ | |
| 4.20 | 2-F | 6-Cl | |
| 4.21 | 3-F | H | |

TABLE 5

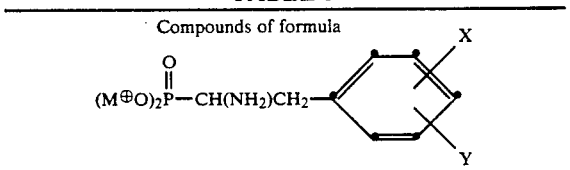

Compounds of formula

| Compound | M$^\oplus$ | X | Y | Physical data |
|---|---|---|---|---|
| 5.1 | Na$^+$ | H | H | m.p. >280° (dec.) |
| 5.2 | ½ Mg$^{++}$ | H | H | |
| 5.3 | ⅓ Al$^{+++}$ | H | H | |
| 5.4 | ½ Mn$^{++}$ | 4-F | H | |
| 5.5 | ½ Ni$^{++}$ | 4-F | H | |
| 5.6 | ⅓ Al$^{+++}$ | 4-F | H | |
| 5.7 | ½ Zn$^{++}$ | 4-F | H | |
| 5.8 | ¼ Zr$^{4+}$ | 4-Cl | H | |
| 5.9 | ½ Mn$^{++}$ | 4-Cl | H | |
| 5.10 | ½ Co$^{++}$ | 4-Cl | H | |
| 5.11 | ⅓ Al$^{+++}$ | 2-Cl | 4-F | |
| 5.12 | ½ Cu$^{++}$ | 2-Cl | 4-F | |
| 5.13 | ½ Cu$^{++}$ | 4-F | H | m.p. >300° (dec.) |
| 5.14 | ⅓ Fe$^{+++}$ | 4-F | H | |
| 5.15 | ½ Ca$^{++}$ | H | 4-OCHF$_2$ | |
| 5.16 | ⅓ Al$^{+++}$ | H | 4-OCHF$_2$ | |
| 5.17 | ½ Cu$^{++}$ | 4-CN | H | |
| 5.18 | ⅓ Al$^{+++}$ | 2-Cl | 6-F | |
| 5.19 | ½ Mn$^{++}$ | 2-Cl | 6-F | |
| 5.20 | ½ Ca$^{++}$ | 2-Me | 4-F | |
| 5.21 | (MeNH$_3$)$^+$ | 4-F | H | m.p. 275–285° (dec.) |
| 5.22 | (isoC$_3$H$_7$NH$_3$)$^+$ | H | CF$_3$ | |

TABLE 5-continued

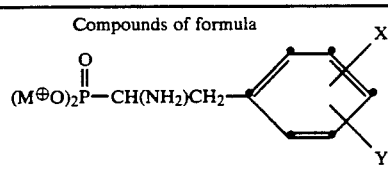

Compounds of formula

| Compound | M$^\oplus$ | X | Y | Physical data |
|---|---|---|---|---|
| 5.23 | (C$_6$H$_5$NH$_3$)$^+$ | 2-Cl | 4-F | |

Formation Examples for Active Ingredients (Compounds) of Formula I (Throughout, Percentages are by Weight)

| F1. Solutions | a) | b) | c) | d) |
|---|---|---|---|---|
| a compound of Tables 1 to 5 | 80% | 10% | 5% | 95% |
| ethylene glycol monomethyl ether | 20% | — | — | — |
| polyethylene glycol 400 | — | 70% | — | — |
| N-methyl-2-pyrrolidone | — | 20% | — | — |
| epoxidised coconut oil | — | — | 1% | 5% |
| petroleum distillate (boiling range 160–190°) | — | — | 94% | — |

These solutions are suitable for application in the form of microdrops.

| F2. Granulates | a) | b) |
|---|---|---|
| a compound of Tables 1 to 5 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| F3. Dusts | a) | b) |
|---|---|---|
| a compound of Tables 1 to 5 | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

| F4. Wettable powders | a) | b) | c) |
|---|---|---|---|
| a compound of Tables 1 to 5 | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixtures is thoroughly ground in a suitable mill, affording wettable powders which can be diluted with water to give suspensions of the desired concentration and which are particularly suitable for seed dressing.

| F5. Emulsifiable concentrate | |
| --- | --- |
| a compound of Tables 1 to 5 | 10% |
| octylphenol polyethlene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water. These emulsions are particularly suitable for seed dressing.

BIOLOGICAL EXAMPLES

Example B1

Action Against *Botrytis cinerea* on Beans

Residual Protective Action

Bean plants about 10 cm in height are sprayed with a spray mixture (0.02%) prepared from a wettable powder formulation of the test compound. After 48 hours the treated plants are infected with a conidia suspension of the fungus. The infected plants are incubated for 3 days at 95–100% relative humidity and 21° C. and then an evaluation of fungus attack is made. Botrytis attack is 100% on untreated, infected bean plants. Attack is less than 20% after treatment with one of the compounds of formula I. No attack (0–5%) is observed after treatment with e.g. compounds 1.5, 2.6, 2.11, 3.4, 2.15, 2.37, 5.13 and others.

Example B2

Action Against *Fusarium nivale* in Rye (Seed Dressing)

Rye seeds of the Tetrahell variety which are naturally infected with *Fusarium nivale* are dressed on a mixer roll with the test fungicide at concentrations of 600 and 200 ppm of active ingredient (based on the weight of the seeds). The infected and treated rye is sown in October in the open with a seeder in plots 3 meters long and in 6 rows. Three replicates are carried out with each test compound at its given concentration. until evaluation is made, the test plants are cultivated under normal field conditions, preferably in a region with unbroken snow cover during the winter months. to evaluate the phytotoxicity, an assessment is made of emergence in the autumn and population density and tillering in the spring. To determine the effectiveness of the test compounds, the percentage of plants attacked by Fusarium is assessed in the spring directly after the snow has melted.

The tested compounds of formula I exhibited scarcely any or no phytoxicity. Compounds 1.5, 1.8, 2.1, 2.2, 2.6, 2.8, 2.34 and others inhibited Fusarium attack completely at both given concentrations.

Example B3

Action Against *Helminthosporium gramineum* on Barley (Seed Dressing)

Seeds of winter barley of the "Cl" variety which are naturally infected with *Helminthosporium gramineum* are processed on a mixer roll with the test Fungicide at concentrations of 600 and 200 ppm of active ingredient (based on the weight of the seeds). The infected and treated barley is sown in October in the open with a seeder in plots 2 meters long and in 3 rows. Three replicates are carried out with each test compound at its given concentration. Until evaluation is made, the test plants are cultivated under normal field conditions. To evaluate the phytotoxicity, an assessment is made of emergence in the autumn and population density and tillering in the spring. To determine the effectiveness of the test compounds, the percentage of stalks attacked by Helminthosporium is assessed at the time of ear emergence.

The test compounds of formula I exhibited scarcely any or no phytotoxicity. At both given concentrations, compounds 1.28, 2.2, 2.6, 2.9, 2.30, 3.5 and others inhibited fungus attack to less than 20% compared with untreated control plants.

Example B4

Action Against *Ustilago nuda* on Barley (Seed Dressing)

Seeds of winter barley of the "RMl" variety which are naturally infected with *Ustilago nuda* are dressed on a mixer roll with the test fungicide at concentrations of 600 and 200 ppm of active ingredient (based on the weight of the seeds). The infected and treated barley is sown in October in the open with a seeder in plots 2 meters long and in 3 rows. Three replicates are carried out with each test compound at its given concentration. Until evaluation is made, the test plants are cultivated under normal field conditions. To determine the effectiveness of the test compounds, the percentage of ears attacked by Ustilago is assessed during flowering.

Compounds 2.6, 2.10, 2.15, 2.19, 5.21 and others reduced fungus attack at both given concentrations to less than 20%.

Example B5

Action Against *Tilletia tritici* (Seed Dressing)

Seeds of winter wheat of the Probus variety which are artificially infected with smut spores of *Tilletia tritici* (3 g of dry spore material per 1 kg of seeds) are dressed on a mixer roll with the test fungicide at concentrations of 600 and 200 ppm of active ingredient (based on the weight of the seeds). The infected and treated wheat is sown in October in the open with a seeder in plots 2 meters long and in 3 rows. Three replicates are carried out with each test compound at its given concentration. Until ear ripening, the test plants are cultivated under normal field conditions. To evaluate the phytotoxicity, an assessment is made of emergence in the autumn and population density and tillering in the spring. To determine the effectiveness of the test compounds, the percentage of ears attacked by *Tilletia tritici* is assessed at the time of ear ripening.

At both given concentrations, compounds of formula I, e.g. 1.5, 2.8, 1.28, exhibited a marked protective action against attack by *Tilletia tritici*, whereby emergence and growth of the wheat plants were favorably promoted.

What is claimed is:

1. A method of controlling phytopathogenic microorganisms in cultivated plants or of protecting said plants from attack by such microorganisms, which comprises applying to said plants, to parts thereof or the locus thereof the compound 1-amino-2-(4-fluorophenyl)ethanephosphonic acid or a salt thereof.

2. A method of controlling phytopathogenic microorganisms in cultivated plants or of protecting said plants from attack by such microorganisms, which comprises applying to said plants, to parts thereof or to the locus thereof the compound 1-amino-2-(4-methylphenyl)ethanephosphonic acid or a salt thereof.

3. A method of controlling phytopathogenic microorganisms in cultivated plants or of protecting said plants from attack by such microorganisms, which comprises applying to said plants, to parts thereof or to the locus thereof the compound 1-amino-2-(4-methoxyphenyl)ethanephosphonic acid or a salt thereof.

* * * * *